US010359364B2

(12) United States Patent
Klinkhammer et al.

(10) Patent No.: US 10,359,364 B2
(45) Date of Patent: Jul. 23, 2019

(54) HYBRID SPECTROPHOTOMETER WITH VARIABLE OPTICAL PATH LENGTH SAMPLING CELL AND METHOD OF USING SAME

(71) Applicant: G6Nine, LLC, Albany, NY (US)

(72) Inventors: Gary P. Klinkhammer, Corvallis, OR (US); Chris J. Russo, Corvallis, OR (US); Donald L. Jackson, Corvallis, OR (US)

(73) Assignee: G6Nine, LLC, Albany, OR (US)

( * ) Notice: Subject to any disclaimer, the term of this patent is extended or adjusted under 35 U.S.C. 154(b) by 910 days.

(21) Appl. No.: 14/562,037

(22) Filed: Dec. 5, 2014

(65) Prior Publication Data

US 2015/0160125 A1    Jun. 11, 2015

Related U.S. Application Data

(60) Provisional application No. 61/912,153, filed on Dec. 5, 2013.

(51) Int. Cl.
| | |
|---|---|
| *G01N 21/05* | (2006.01) |
| *G01N 21/33* | (2006.01) |
| *G01N 21/64* | (2006.01) |
| *G01N 21/59* | (2006.01) |
| *G01N 21/03* | (2006.01) |
| *G01N 33/18* | (2006.01) |
| *G01N 21/94* | (2006.01) |

(52) U.S. Cl.
CPC ....... *G01N 21/645* (2013.01); *G01N 21/0303* (2013.01); *G01N 21/05* (2013.01); *G01N 21/59* (2013.01); *G01N 21/94* (2013.01); *G01N 33/18* (2013.01); *G01N 2021/6482* (2013.01); *G01N 2021/6484* (2013.01)

(58) Field of Classification Search
CPC .. G01N 21/645; G01N 21/0303; G01N 21/05; G01N 21/59; G01N 33/18; G01N 21/94; G01N 2021/6482; G01N 2021/6484
USPC .................................................. 250/227.23
See application file for complete search history.

(56) References Cited

U.S. PATENT DOCUMENTS

| | | | | |
|---|---|---|---|---|
| 4,323,918 | A * | 4/1982 | Bendell | H04N 9/097 348/265 |
| 5,835,645 | A | 11/1998 | Jorgenson et al. | |
| 5,920,667 | A | 7/1999 | Tiao et al. | |
| 6,069,694 | A * | 5/2000 | VonBargen | G01N 21/05 356/246 |
| 7,518,720 | B2 * | 4/2009 | Kolp | G01N 21/09 356/244 |
| 7,894,061 | B2 | 2/2011 | MacDougall et al. | |
| 2011/0102790 | A1 * | 5/2011 | Haught | G01J 3/02 356/319 |
| 2012/0205547 | A1 * | 8/2012 | Klinkhammer | G01N 21/0303 250/373 |

* cited by examiner

*Primary Examiner* — Seung C Sohn
(74) *Attorney, Agent, or Firm* — Bejin Bieneman PLC

(57) ABSTRACT

A hybrid spectrophotometric instrument utilizing absorption and fluorescence observations requires different cell parameters for optimal performance. The ability to have an instrument with a variable optical path length with a single set of optical surfaces and one detector to reduce system variance is unique. A Zero Angle Photon Spectrometer with the additional hardware and software to support a variable path length instrument is described.

16 Claims, 8 Drawing Sheets

US 10,359,364 B2

HYBRID SPECTROPHOTOMETER WITH VARIABLE OPTICAL PATH LENGTH SAMPLING CELL AND METHOD OF USING SAME

CROSS REFERENCE TO RELATED APPLICATIONS

This application is related to and claims priority to U.S. Provisional Patent Application number 61/912,153 filed on Dec. 5, 2013.

BACKGROUND

Waters have been monitored spectrophotometrically for many years. However, generally only one chemical or physical parameter was measured at a time, and measurements were generally made using a single optical technique, such as light scattering for turbidity or fluorescence for chlorophyll-a. Typically, water monitoring occurs sporadically by occasional field sampling, which is taken to a laboratory for analysis. Some specialized sensors have been used on water flowing through a pipe, which provide real-time measurement of one component of the water. Generally it is desirable to move laboratory instruments to the field to perform continuous on-line water monitoring but such monitoring has been for a very limited number of water components. Typically, measurement of multiple components using more than one optical technique has required multiple sensors. This approach requires a skilled operator capable of performing multiple calibration and maintenance procedures. Multiple sensors also propagate errors from each device, which limits the monitoring system's ability to accurately detect anomalies or events using a combination of readings.

Several relationships have been established in the art. The Beer-Lambert Law relates to absorbance readings. This is most often used in a quantitative way to determine concentrations of an absorbing species in solution:

$$A = \log_{10}(I_0/I) = \varepsilon l c$$

where A is the measured absorbance, $I_0$ is the incident light intensity at a given wavelength, I is the transmitted light intensity, l the path length through the sample, and c the concentration of the absorbing species. For each species and wavelength, $\varepsilon$ is a constant known as the molar absorptivity or extinction coefficient. This constant is a fundamental molecular property in a given solvent, at a particular temperature and pressure, and has units of 1/M*cm or often AU/M*cm.

The Beer-Lambert Law predicts a linear relationship between absorption and concentration and is useful for characterizing many compounds but does not hold as a universal relationship. A second order polynomial relationship between absorption and concentration is sometimes encountered for very large, complex molecules or simpler compounds at relatively high concentration. The Beer-Lambert law has implicit assumptions that must be met experimentally for it to apply. For instance, the chemical makeup and physical environment of the sample can alter its extinction coefficient. The chemical and physical conditions of a test sample therefore must match reference measurements for conclusions to be valid. The Beer-Lambert law also only applies to pure solutions and unencumbered absorbance. In the real world, scattering from particles and non-specific absorption contribute to measured values. The ability to measure the sample at multiple optical path lengths allows the molecular absorptivity to be calculated directly for the sample being evaluated at the wavelength being used.

One apparatus for measuring the purity of fluids is known from the disclosure of U.S. Pat. No. 8,102,518 to Haught et al. Devices used for measuring fluid purity in general, and for identifying and quantifying the amount of impurities in particular, commonly use light as a probing mechanism. Such devices are generally referred to as photometers. A specific type of photometer is the spectrophotometer, which permits adjustment of the light frequency (i.e., Wavelength), for making measurements at multiple frequencies. An optical sample cell contains a portion of fluid being analyzed at any given moment.

Electromagnetic energy that is used to irradiate the aqueous stream may either be rejected by material in the aqueous stream, transmitted through the aqueous stream and its material load, or absorbed by the aqueous stream material. In the instance where the electromagnetic energy is absorbed by the aqueous stream material, the aqueous stream material may also fluoresce. In devices used to measure purity, one of three basic measurement methodologies following from these potential interactions of the electromagnetic energy with the aqueous stream is generally employed. These methodologies measure the parameters absorption, reflectance, and fluorescence of the aqueous stream in the optical sample cell. In accomplishing the various methodologies, an electromagnetic energy detector has been disposed with respect to an electromagnetic energy transmitter so that the detector is optimally positioned to be responsive to the associated parameter.

DESCRIPTION

Figure 1A:
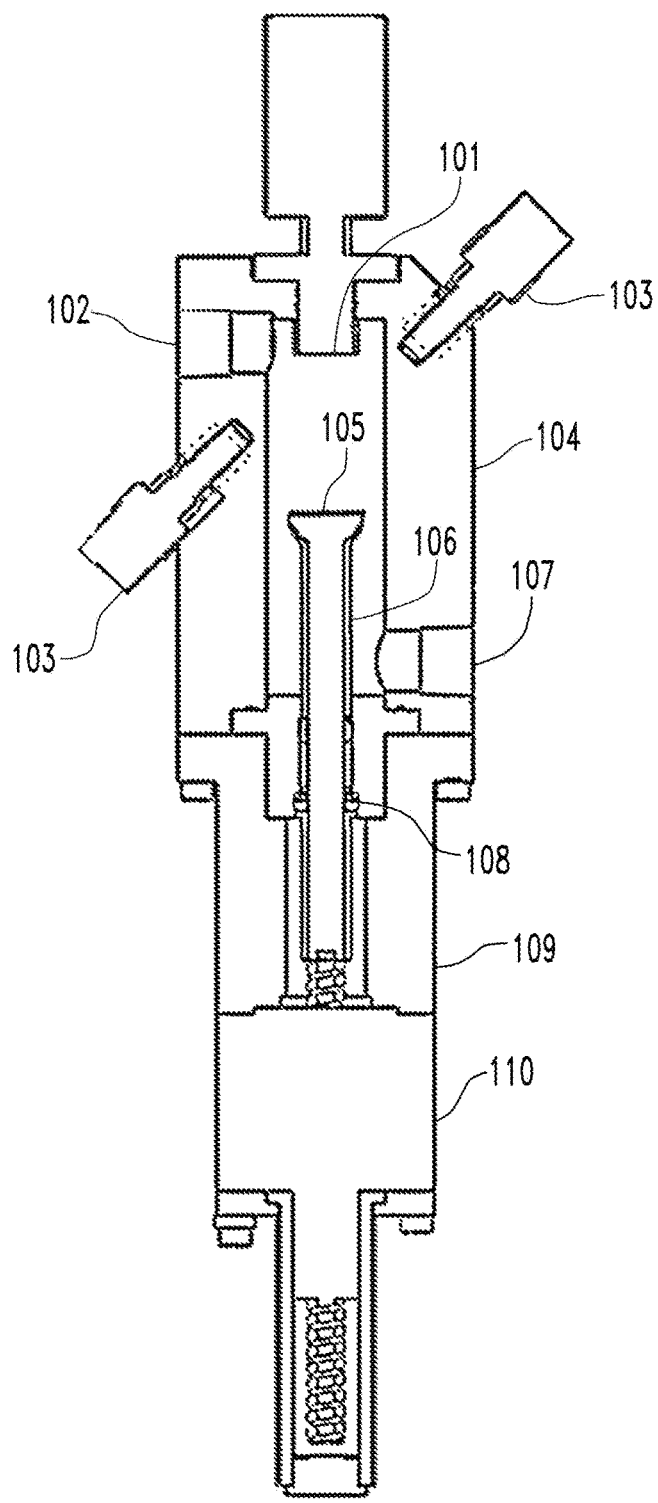
FIG. 1A is a cross-sectional view of one example of an apparatus which can provide a continuously variable path length over a specified distance.

For the purposes of promoting an understanding of the principles of the claimed technology and presenting its currently understood best mode of operation, reference will now be made to the embodiments illustrated in the drawings and specific language will be used to describe the same. It will nevertheless be understood that no limitation of the scope of the claimed technology is thereby intended, with such alterations and further modifications in the illustrated device and such further applications of the principles of the claimed technology as illustrated therein being contemplated as would normally occur to one skilled in the art to which the claimed technology relates.

Figure 1B:
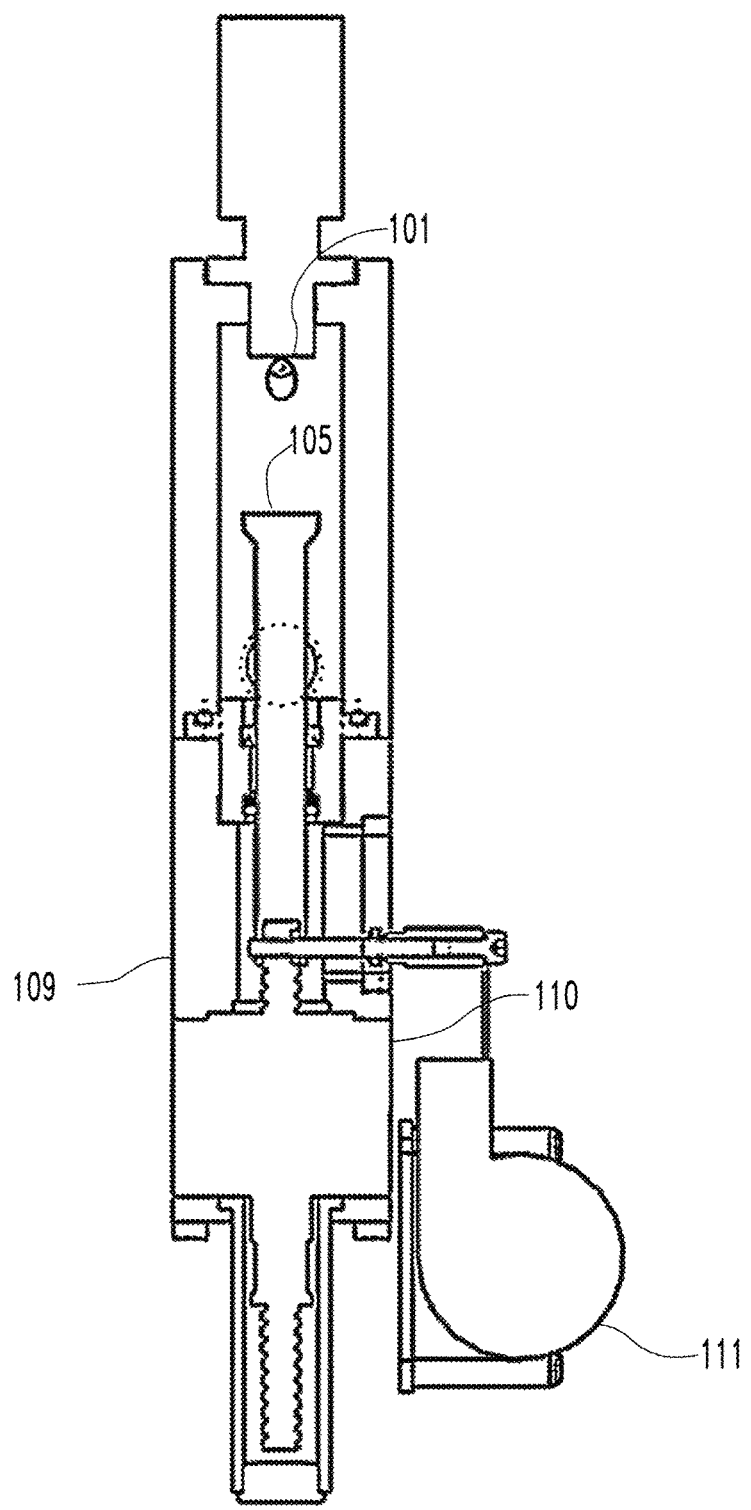
FIG. 1B is a cross-sectional side view the apparatus shown in FIG. 1A.
Figure 2:
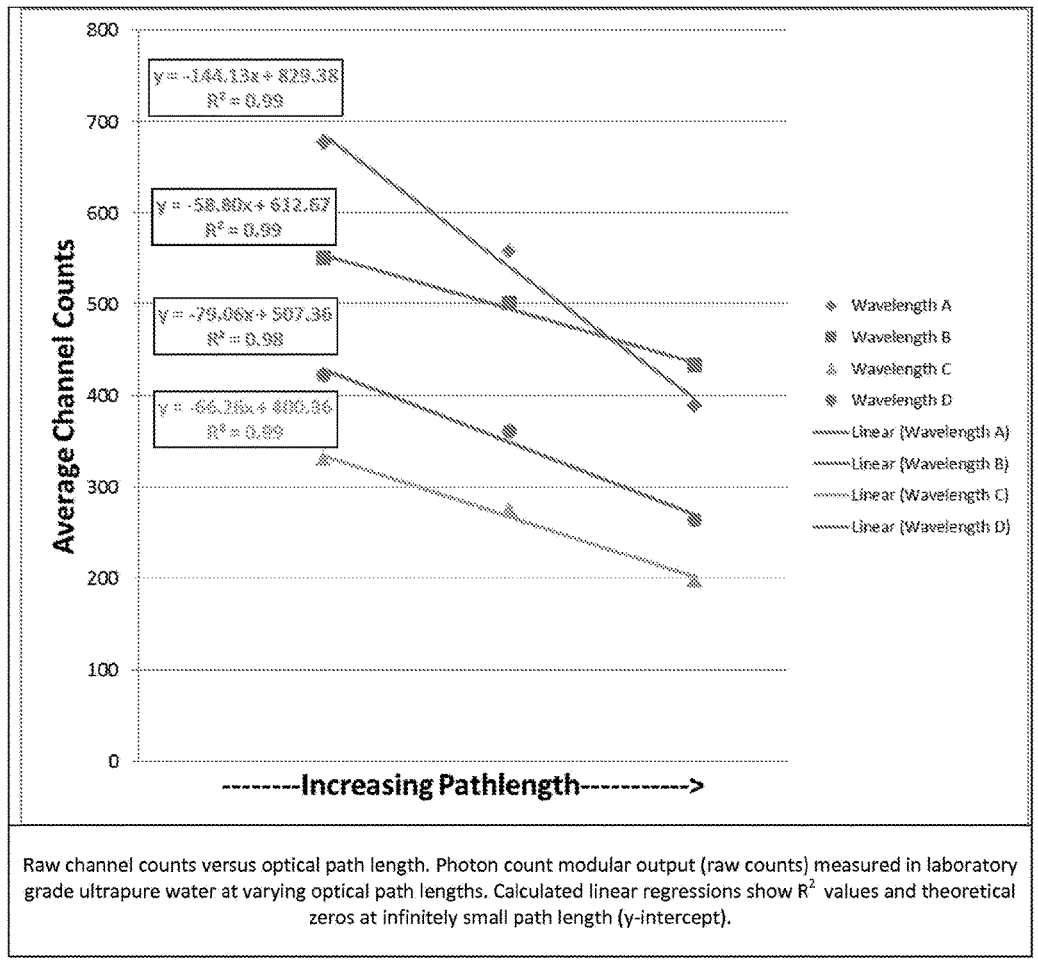
FIG. 2 is a chart showing the correlation between optical path length and the transmitted light for several wavelengths.
Figure 3:
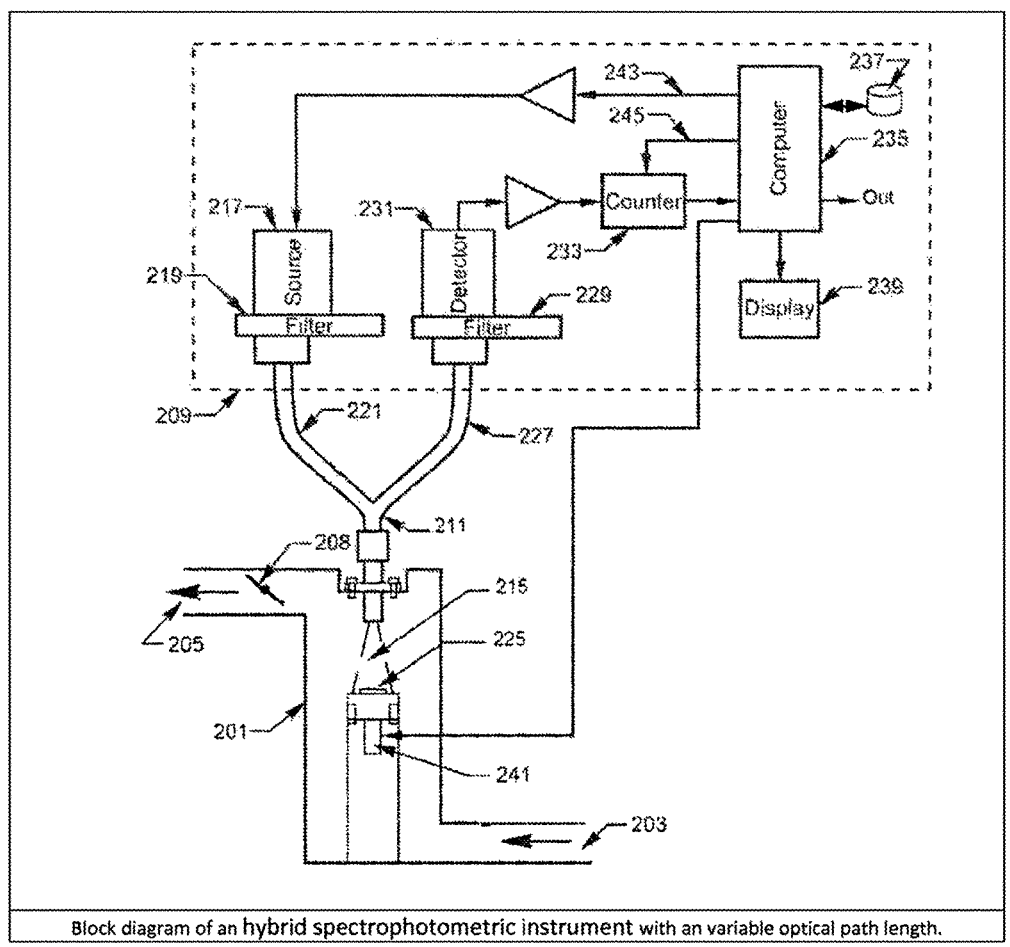
FIG. 3 is a block diagram of one example of a hybrid spectrophotometric instrument with a variable optical path length.

FIG. 1 Key
101 fiber optic bundle—common end
102 sample outlet—flow cell
103 cleaning nozzles
104 flow cell
105 reflective target
106 target support
107 sample inlet—flow cell
108 fluid seal
109 flow cell motor adaptor
110 motor
111 position transducer FIG. 3 Key
201 flow cell
203 sample inlet, flow cell
205 sample outlet, flow cell
208 isolation valve
209 electronics enclosure
211 fiber optic bundle, common end
215 illuminated fluid
217 power supply and broad spectrum light source
219 illumination computer controlled optical filter wheel
221 fiber optic bundle, illumination branch
225 reflective target, moonbeam lens
227 fiber optic bundle, detector branch
229 detector computer controlled optical filter wheel
231 detector
233 digital computer controlled counter
235 embedded computer
237 local storage (optional)
239 local display (optional)
241 computer controlled stepper motor
243 trigger control for light source
245 window/enable control for optical detector
248 LAN, wireless communication device, modem, or other communication means (optional)

The present invention is an enhancement of an integrated spectrophotometric system for monitoring changes in a fluid system such as that described in U.S. Pat. No. 8,102,518 to Haught, et al. It is understood that the disclosed technology could also be adapted to work with other examples of spectrophotometric systems. For example, the disclosed system could also be adapted for use with the zero angle photon spectrometers described in U.S. Pat. Nos., 5,304,492; 7,411,668 B2; 8,102,518 B2; and U.S. Patent Application 2012/0205547. The disclosed technology could also be adapted and used with other suitable spectrophotometric systems.

In one example, the disclosed technology can be used as an in-line, on-line instrument for monitoring various chemical parameters in a fluid system on a continuous or intermittent basis, such as for water flowing by a monitoring station containing the disclosed technology. Such a system may be used for monitoring natural, drinking, purified, or wastewaters from industrial or municipal facilities for routine screening and as an indicator of changes in the water. In one example the instrument has an on board computer 235 which runs through a programmed sequence which: cycles through a set of optical filter pairs and records the values, performs calculations using those values to generate statistical information of those readings, uses calculated results to generate client results, sends all or a subset of this data to the client by using a local area network, a 4 to 20 mA current signal, or a cellular modem to a remote, secure server which a user can access. Optionally, all raw counts, calculated results, and statistical information may be saved on a local hard drive or other storage device to be collected later.

In this particular example, the fixed optical path length base, mirror support, and mirror have been removed from the new flow cell and replaced with a optical reflective target 105, reflective target support 106, fluid seal 108, flow cell/motor adapter 109, linear servo motor 110, and a linear position transducer 111, as one example of how to implement a variable path length hybrid spectrophotometric instrument. The servo motor is controlled by the embedded computer 235 and the position transducer is monitored by the computer 235. In one embodiment there are hard stops at the minimum and maximum distance for the lens assembly. The instrument tracks the position of the lens assembly by maintaining a record of the number of steps the motor has taken from the home position and checks this position with the output of the linear position transducer. The transducer is repeatable to 0.1 mm. If the calculated position and the measured position do not match, the computer 235 will re-home the lens assembly. The home position may also be checked on a periodic basis.

Another embodiment of an analytical instrument for the determination of impurities in an aqueous stream which may employ the present invention will now be described. The aqueous stream to be analyzed could be a municipal water supply, industrial effluent, groundwater, and the like. In one embodiment, an aqueous sample is caused to flow through an optical sample cell from an inlet to an outlet. Valves may be controlled to regulate the flow rate of aqueous stream through the optical sample cell, particularly if the stream is to be intermittent, reduced, or combined at certain times. Optical components and electronics are optically connected to the optical sample cell through an optical fiber bundle. A narrowband electromagnetic energy source for supplying an illumination probe to the aqueous stream, in an embodiment utilizes a source of electromagnetic energy such as a flash lamp. Light (a portion of electromagnetic radiation occurring within wavelengths including infrared, visible light, and ultraviolet light) is directed by the system through a bandpass optical filter to select a desired wavelength and passed into and through a portion of an optical fiber assembly to the optical sample cell. The light is then directed, as the illumination probe, through the aqueous sample in the optical sample cell and reflected from a light reflector disposed in the optical sample cell, through the aqueous sample again, and back into the optical fiber bundle. A separate portion of the optical fiber bundle directs the returning light through another bandpass optical filter and is detected by an optical detector.

Signals from detector are coupled to a counter and then to a computer. The computer may be, alternatively, a programmed general-purpose computer or a specialized computer controller to control the movement of a positioning motor (capable of repositioning light reflector), valves (if any), optical filters, etc. Signals from the optical detector are received, recorded, and analyzed by the computer and the results are stored in a memory, reported on a display, and/or output to external devices, or signals are fed back to affect appropriate change in the sensor system or fluid control system as a feedback loop. Further, algorithms may be stored in memory to be recalled and executed by the computer to extract desired information from the data collected.

EXAMPLES

Several test runs were generated using a spectrophotometric system according to the disclosed technology. The path length was varied from 3.0 cm to 5.0 cm in 0.5 cm increments. The instrument was set up to measure 15 sequential sets of data for the 10 different filter pairs at each path length. Seven filter pairs established an absorbance measurement condition and three established a fluorescent measurement condition. Each of the 150 represented measurements in this 20 minute block represents an average of 400 individual measurements. Only four of the 10 different measurements are shown in FIGS. 4A through 7. The measured photon counts were then used to calculate the absorbance for each of the absorbance filter pairings using the counts and the path length. The raw counts were used as an indication of background counts in the fluorescent filter pairings. Treated city drinking water was routed through the instrument while this data was generated. This source is constant and typically has low levels of material which show an optical signature over this time interval.

Figure 4A:
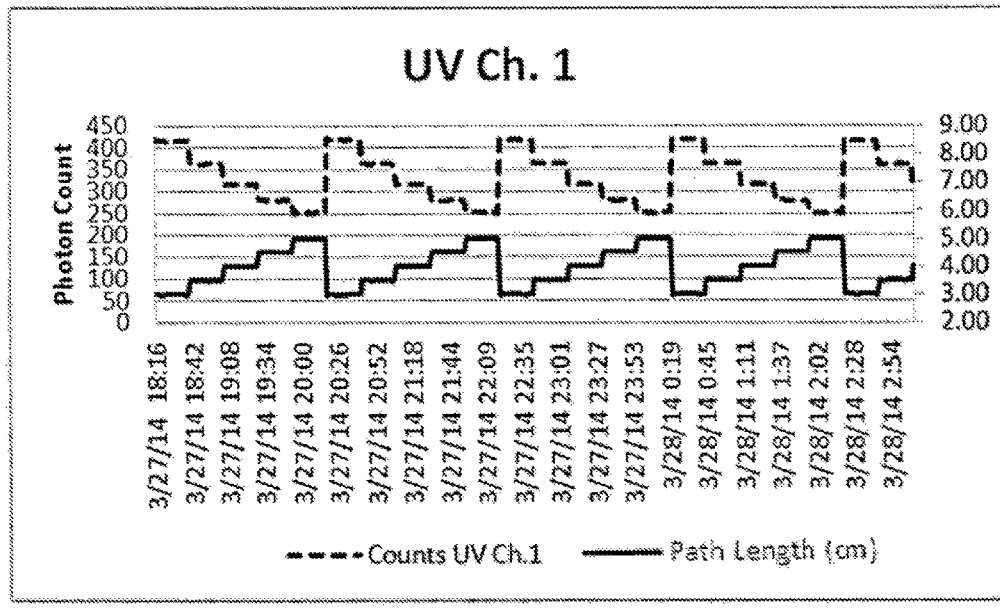
FIG. 4A is a chart showing the relationship of the counts for a Ultra Violet electromagnetic signal, in photon counts and the optical path length in centimeters.
Figure 4B:
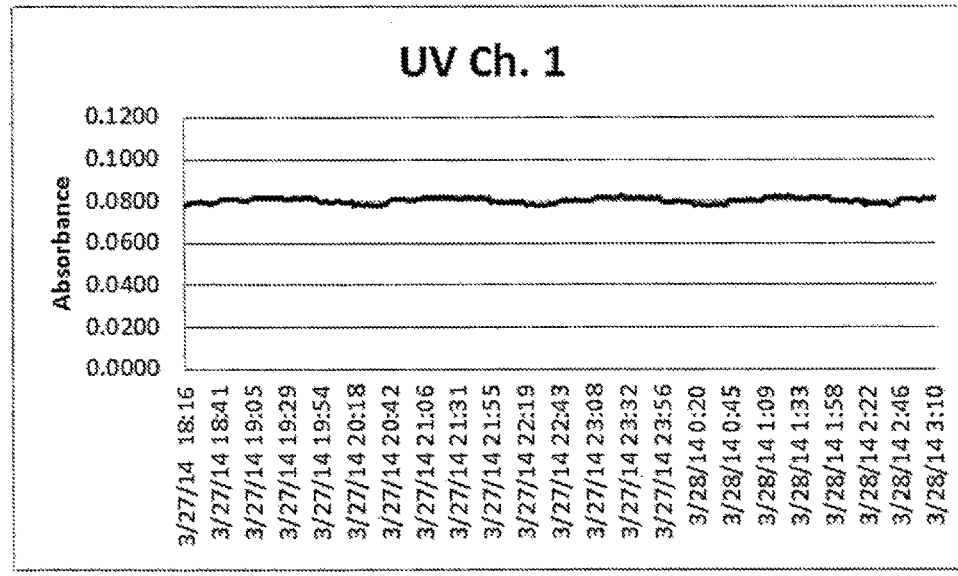
FIG. 4B is a chart which shows the calculated absorbance using Beer-Lambert equation, using the values from FIG. 4A as input values.
Figure 5A:
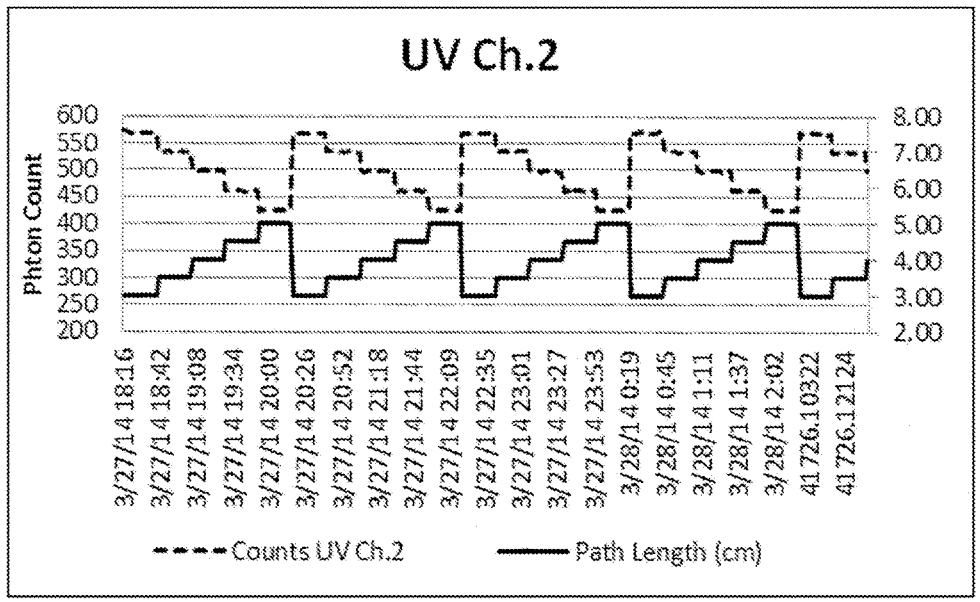
FIG. 5A is a chart showing the relationship of the counts for an ultra violet electromagnetic signal at a wavelength different from FIG. 4A.
Figure 5B:
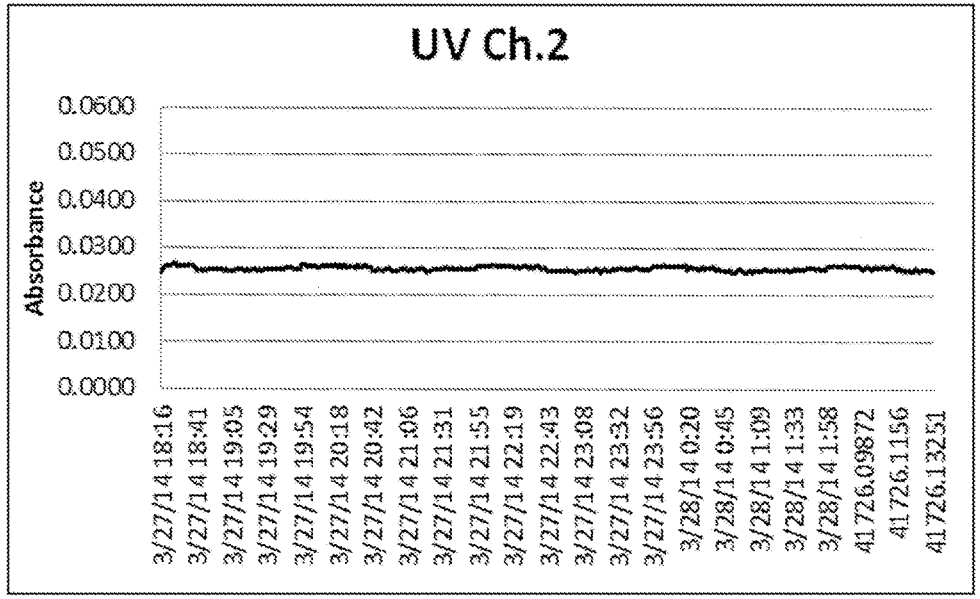
FIG. 5B is a chart which shows the calculated absorbance using Beer-Lambert equation, using the values from FIG. 5A as input values.
Figure 6A:
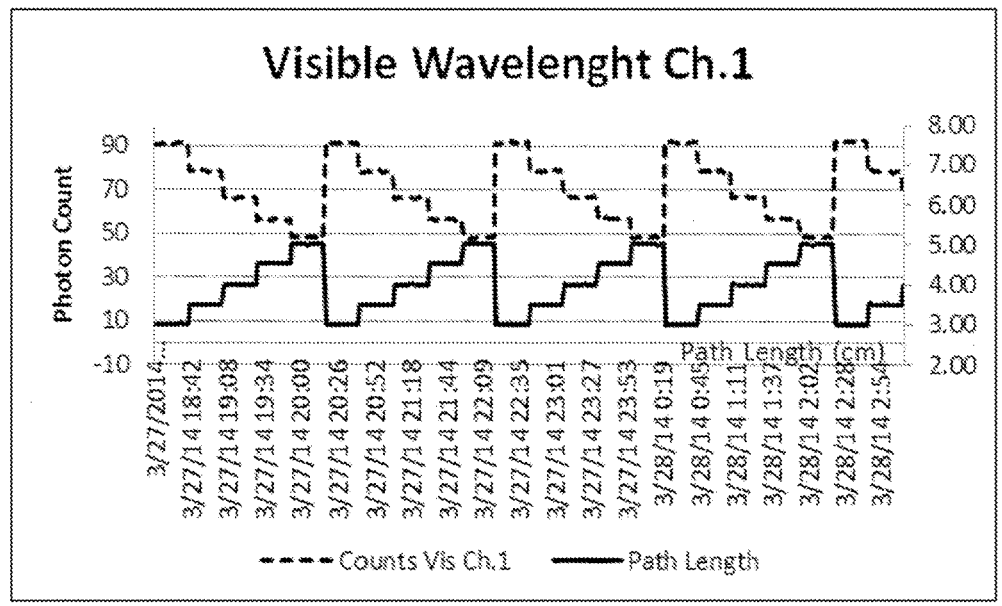
FIG. 6A is a chart showing the relationship of the counts for a visible electromagnetic signal, in photon counts and the optical path length in centimeters.
Figure 6B:
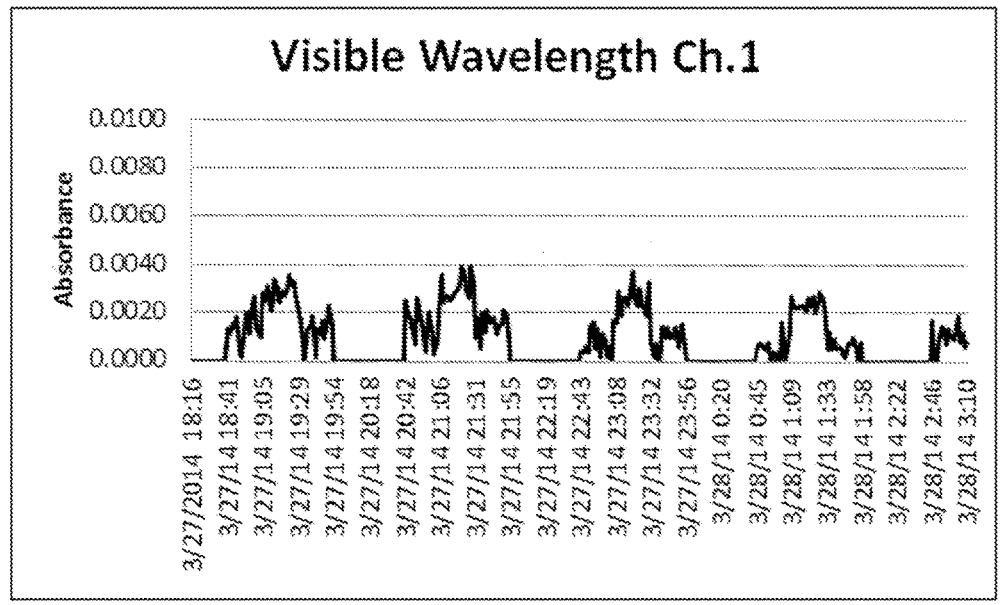
FIG. 6B is a chart which shows the calculated absorbance using Beer-Lambert equation, using the values from FIG. 6A as input values.

In FIGS. 4A, 5A, 6A, and 7 the solid lines indicate the programmed path length (scale on the right) at which measurements took place. The dashed line indicates the photon count values (scale to the left) measured for various wavelengths and spectrophotometric techniques at each programmed path length. In FIGS. 4B, 5B, 6B the line is the calculated absorbance at a particular point in time using obtained values for path length and photon counts. Over an eight hour test period the spectrophotometric system recorded approximately 330 results for each of 10 wavelengths (filter pairs), with each of those being the average value for 400 measurements.

The absorption measurements shown in FIGS. 4B, 5B, and 6B demonstrate the ability of the disclosed technology to accurately reposition a spectrophotometric instrument's optics at a desired path length. The diagrams also demonstrate the disclosed technology's ability to accurately and precisely track zero values at various wavelengths against which low (FIG. 4), very low (FIG. 5) and near detection (FIG. 6) values of absorption are determined. The ability to optimize the path length for individual wavelengths enhances the disclosed technology's ability to analyze at the most appropriate path length for each wavelength as dictated by a matrix of interest (short path lengths at wavelengths with strong absorptive properties and longer path lengths at wavelengths with weak absorptive properties).

Figure 7:
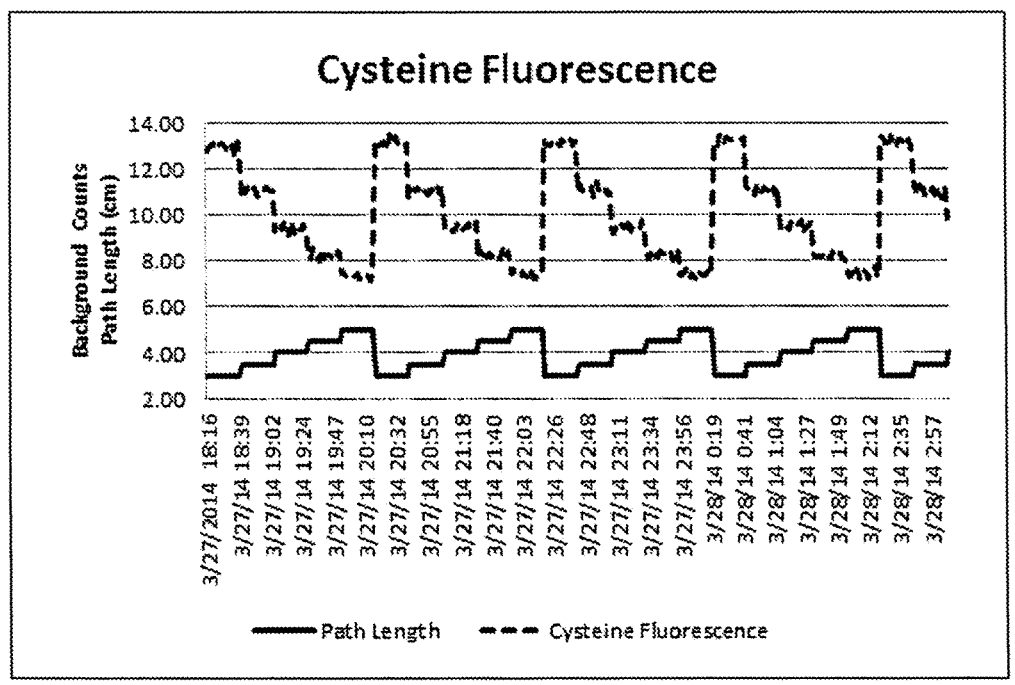
FIG. 7 is a chart showing the cysteine fluorescence signal, when there is no cysteine material in the fluid.

The fluorescence measurements shown in FIG. 7 illustrate the ability of the disclosed technology to enhance fluorescence measurements by allowing a device to operate at maximum path length thus reducing the background values used during fluorescence measurements. The reduction of background (or scattered) light in fluorescence measurements is directly proportional to the signal to noise ratio, a critical limitation of such measurements. These cysteine fluorescence measurements were made with no fluorescent material in the fluid being measured.

Variable path length technology allows hybrid spectrophotometric analyzers to be optimized by allowing the system to work at optimized path length depending on the absorptive properties of the matrix of interest while also allowing background light to be minimized during fluorescence measurements. These data demonstrate several advantages continuous path length technology has over both fixed and multiple path length devices.

While the claimed technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the claimed technology are desired to be protected.

What is claimed is:

1. An optical sensor for determining multiple optical parameters of a fluid flowing through the sensor comprising:
   a flow cell having a fluid inlet, a fluid outlet, and a light path which passes through a portion of fluid in the flow cell;
   a light emitting system comprising a wavelength selection system capable of sequentially selecting a plurality of particular wavelengths of light from the light emitting system;
   a fiber optical bundle capable of transmitting light from the light emitting system to the light path and receiving light from the fluid flowing through the flow cell;
   an optical reflective target capable of reflecting light passing through fluid in the fluid cell back to the fiber optical bundle;
   an optical detector capable of detecting each of the plurality of particular wavelengths of light from the light emitting system; and
   a linear servo motor and a linear position transducer designed to adjust the length of said light path;
   wherein the length of said light path is defined by the distance between said fiber optical bundle and said optical reflective target.

2. The optical sensor of claim 1, further comprising a second wavelength selection system capable of sequentially selecting a plurality of particular wavelengths of light returning from the flow cell.

3. The optical sensor of claim 1, wherein the length of said light path is adjustable by increasing or decreasing the distance between said fiber optical bundle and said optical reflective target.

4. The optical sensor of claim 1, wherein the length of said light path is adjustable by moving said optical reflective target relative to said fiber optical bundle.

5. The optical sensor of claim 1, wherein the length of said light path is adjustable by moving said fiber optical bundle relative to said optical reflective target.

6. The optical sensor of claim 1, wherein the length of said light path is adjustable by moving both said fiber optical bundle and said optical reflective target.

7. The optical sensor of claim 1, wherein the linear position transducer is outside the flow cell.

8. The optical sensor of claim 1, wherein the linear position transducer is spaced from the flow cell.

9. An optical sensor for measuring impurities in an aqueous stream, comprising:
   a light source capable of producing a plurality of discrete wavelengths of light;
   a flow cell through which an aqueous stream is routed;

a fiber optical bundle capable of transmitting light produced by said light source into said flow cell and through said aqueous stream to generate a sample signal;

a reflective target disposed within said flow cell and capable of reflecting said sample signal;

a light path which passes through a portion of said flow cell and which is defined as the distance between said fiber optical bundle and said reflective target within said flow cell;

an optical detector capable of detecting said sample signal and operationally connected to a computer to calculate a value of an impurity from said sample signal; and a linear servo motor and a linear position transducer designed to adjust the length of said light path.

10. The optical sensor of claim 9, wherein the light path is adjusted by moving the reflective target relative to the fiber optical bundle.

11. The optical sensor of claim 9, wherein the light path is adjusted by moving the fiber optical bundle relative to the reflective target.

12. The optical sensor of claim 9, wherein the linear position transducer is outside the flow cell.

13. The optical sensor of claim 9, wherein the linear position transducer is spaced from the flow cell.

14. An optical sensor for determining impurities in a fluid flowing through the sensor comprising:

a flow cell having a fluid inlet, fluid outlet and a light path that passes through a portion of the fluid in the flow cell;

a light emitting system;

a wavelength selection system for sequentially selecting a plurality of particular wavelengths of light from the light emitting system;

a fiber optical bundle for transmitting light from the light emitting system to the light path, through the fluid and receiving light from the fluid flowing through the flow cell;

a reflective target disposed within said flow cell and capable of reflecting wavelengths of light emitted from said light emitting system;

an optical detector for detecting each of the plurality of particular wavelengths of light being received; and a linear servo motor and a linear position transducer designed to move said reflective target within said flow cell.

15. The optical sensor of claim 14, wherein the linear position transducer is outside the flow cell.

16. The optical sensor of claim 14, wherein the linear position transducer is spaced from the flow cell.

* * * * *